United States Patent [19]
Smith et al.

[11] Patent Number: 5,415,868
[45] Date of Patent: May 16, 1995

[54] CAPLETS WITH GELATIN COVER AND PROCESS FOR MAKING SAME

[75] Inventors: Floyd S. Smith, Kalamazoo; Mark E. Crim, Allegan, both of Mich.

[73] Assignee: L. Perrigo Company, Allegan, Mich.

[21] Appl. No.: 74,064

[22] Filed: Jun. 9, 1993

[51] Int. Cl.⁶ .................................... A61K 9/48
[52] U.S. Cl. .................................... 424/454; 424/451; 424/452; 424/453; 424/456; 424/478; 53/419; 53/441; 53/454; 53/471
[58] Field of Search .............. 53/419, 441, 471, 454; 424/451, 452, 453, 454, 456, 478

[56] References Cited

U.S. PATENT DOCUMENTS

| | | | |
|---|---|---|---|
| 1,520,940 | 12/1924 | Dulitz | 215/246 |
| 1,657,982 | 1/1928 | Wilkie et al. | 264/307 |
| 1,685,392 | 9/1929 | Beadle | 426/125 |
| 1,774,258 | 8/1930 | English | 206/222 |
| 1,931,765 | 10/1933 | Leever | 53/3 |
| 2,663,130 | 12/1953 | Donofrio | 53/89.5 |
| 3,983,258 | 9/1976 | Weaver | 426/307 |
| 4,793,119 | 12/1988 | Maso | 53/139.3 |
| 4,820,524 | 4/1989 | Berta | 424/474 |
| 4,844,906 | 7/1989 | Hermelin et al. | 424/454 |
| 4,867,983 | 9/1989 | Berta | 424/451 |
| 4,928,840 | 5/1990 | Barshay et al. | 220/8 |
| 4,936,074 | 6/1990 | Graham | 53/440 |
| 4,966,771 | 10/1990 | Berta | 424/478 |
| 4,973,480 | 11/1990 | Hermelin et al. | 424/454 |
| 5,074,426 | 12/1991 | Goodhart et al. | 220/4.24 |
| 5,085,033 | 2/1992 | Graham | 53/436 |
| 5,089,270 | 2/1992 | Hampton et al. | 424/465 |
| 5,146,730 | 9/1992 | Sadek et al. | 53/454 |
| 5,188,688 | 2/1993 | Boardman et al. | 156/69 |
| 5,213,738 | 5/1993 | Hampton et al. | 264/113 |

*Primary Examiner*—Thurman K. Page
*Assistant Examiner*—James M. Spear
*Attorney, Agent, or Firm*—Price Heneveld Cooper DeWitt & Litton

[57] ABSTRACT

Disclosed is a novel simulated capsule medicament consisting of a solid core covered with two shrink-wrapped, hard-shell gelatin capsule halves. The solid cores are covered with the hard-shell gelatin capsule halves by individually shrink-wrapping onto first one end of the core a first hard-shell gelatin capsule half and then individually shrink-wrapping onto a second end of the core a second hard-shell gelatin capsule half.

11 Claims, 2 Drawing Sheets

CAPLETS WITH GELATIN COVER AND PROCESS FOR MAKING SAME

FIELD OF THE INVENTION

The present invention relates to medicaments and processes for providing gelatin coverings for such medicaments.

BACKGROUND OF THE INVENTION

Drug delivery systems are available in a great variety of shapes and forms, among the most common of which are coated compressed hard tablets, caplets and filled gelatin capsules. The use of gelatin capsules for the encapsulation of medicinal agents has been a popular method for administering drugs because many patients prefer to swallow capsules and caplets rather than tablets.

Caplets are solid, oblong tablets which, although very popular as a drug delivery vehicle, have not reached the same level of consumer acceptance gelatin capsules once had. To solve this problem, the pharmaceutical industry has sought to combine the consumer acceptance of a capsule shape with a caplet.

Several proposals have suggested forming caplets and subsequently coating them to simulate a capsule-like medicament. One such proposal is represented by U.S. Pat. Nos. 5,089,270 and 5,213,738 assigned to the present assignee. Other proposals are represented by U.S. Pat. Nos. 4,820,524; 4,928,840 and 5,146,730. None of these proposals contemplate producing capsule-like medicaments by individually covering first one end of a caplet with a hard shell capsule half and shrinking the capsule half onto the caplet, and then covering the other end of each caplet with a second hard shell capsule half and shrinking the capsule half onto the caplet, without contacting the first shrink-wrapped capsule half, to form a gelatin covered caplet.

SUMMARY OF THE INVENTION

The present invention thus provides a novel simulated capsule medicament consisting of a solid core, such as a caplet, covered with two shrink-wrapped, hard-shell gelatin capsule halves. The solid cores are covered with the hard-shell gelatin capsule halves by individually shrink-wrapping onto first one end of the core a first hard-shell gelatin capsule half and then individually shrink-wrapping onto a second end of the core a second hard-shell gelatin capsule half. The two shrink-wrapped capsule halves preferably abut, but do not overlap, at a point about midway of a longitudinal axis of the medicament. Any gap between the two shrink-wrapped capsule halves may be covered by transverse banding the covered caplet with a standard gelatin band. In one embodiment, the two shrink-wrapped hard-shell gelatin capsule halves may be of different colors to form a simulated two color, capsule-like medicament.

DETAILED DESCRIPTION OF THE INVENTION

The basic components of the present medicament include first and second hard-shell gelatin capsule halves, such as commercially marketed by R. P. Scherer Corporation, Troy, Mich. The diameter and lengths of the halves are selected so that they are not slip-fit joinable and then allow a medicinal caplet for oral administration to fit within the capsule halves. The hard gelatin capsule halves can be any size from 4 to 000 and preferably the capsule halves contain different colored gelatin to facilitate the simulation of a capsule medicament.

The medicinal caplet can contain any of the many medicinals presently marketed over-the-counter or on a prescription basis such as aspirin, acetaminophen and ibuprofen. Other well-known medicinals, such as antihistamines and decongestants can be included as well.

Figure 1:
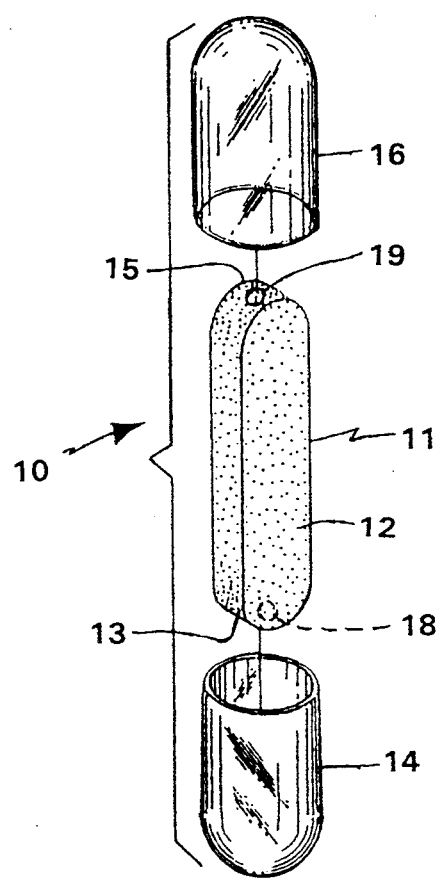
FIG. 1 is an exploded view of the shrink-wrapped hard-shell gelatin capsule covered dosage form of the present invention.
Figure 2:
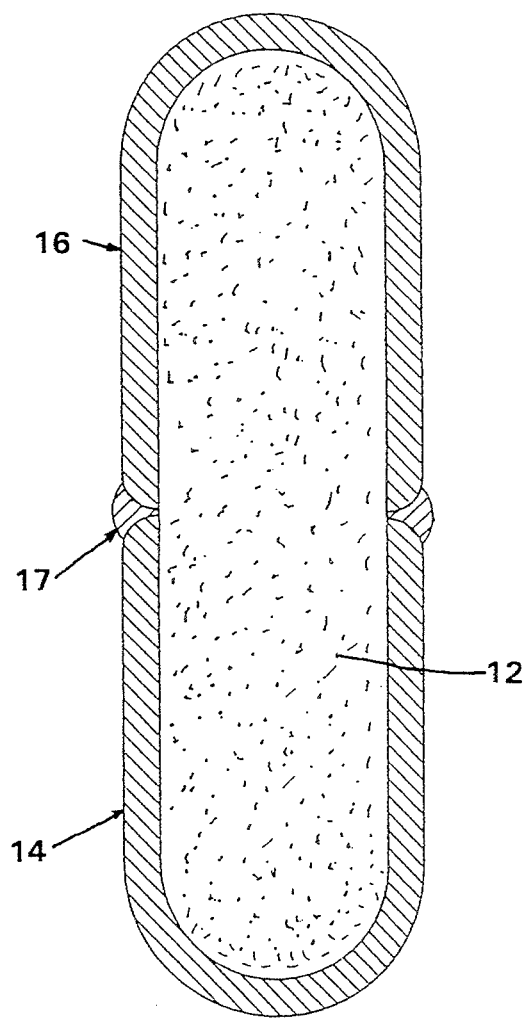
FIG. 2 is a cross-sectional view along the elongated axis of an alternative embodiment of the shrink-wrapped hard-shell gelatin capsule covered dosage form of the present invention.

The present invention provides a simulated gelatin capsule medicament 10. As shown in FIGS. 1 and 2, medicament 10 comprises a caplet-shaped core 12 covered with a pair of hard-shell gelatin capsule halves 14 and 16. Capsule halves 14 and 16 have a combined length of less than or equal to the length of core 12. That is, when capsule halves 14 and 16 are slipped onto core 12, their ends may abut, but will not overlap. Overlapping of the ends is also prevented since capsule halves 14 and 16 are of the same diameter. In a preferred embodiment, hard-shell capsule halves 14 and 16 each having the same length are placed onto core 12. In this embodiment, the annular ends of capsule halves 14 and 16 abut each other at a point about midway 11 of the longitudinal axis of core 12.

Figure 3:
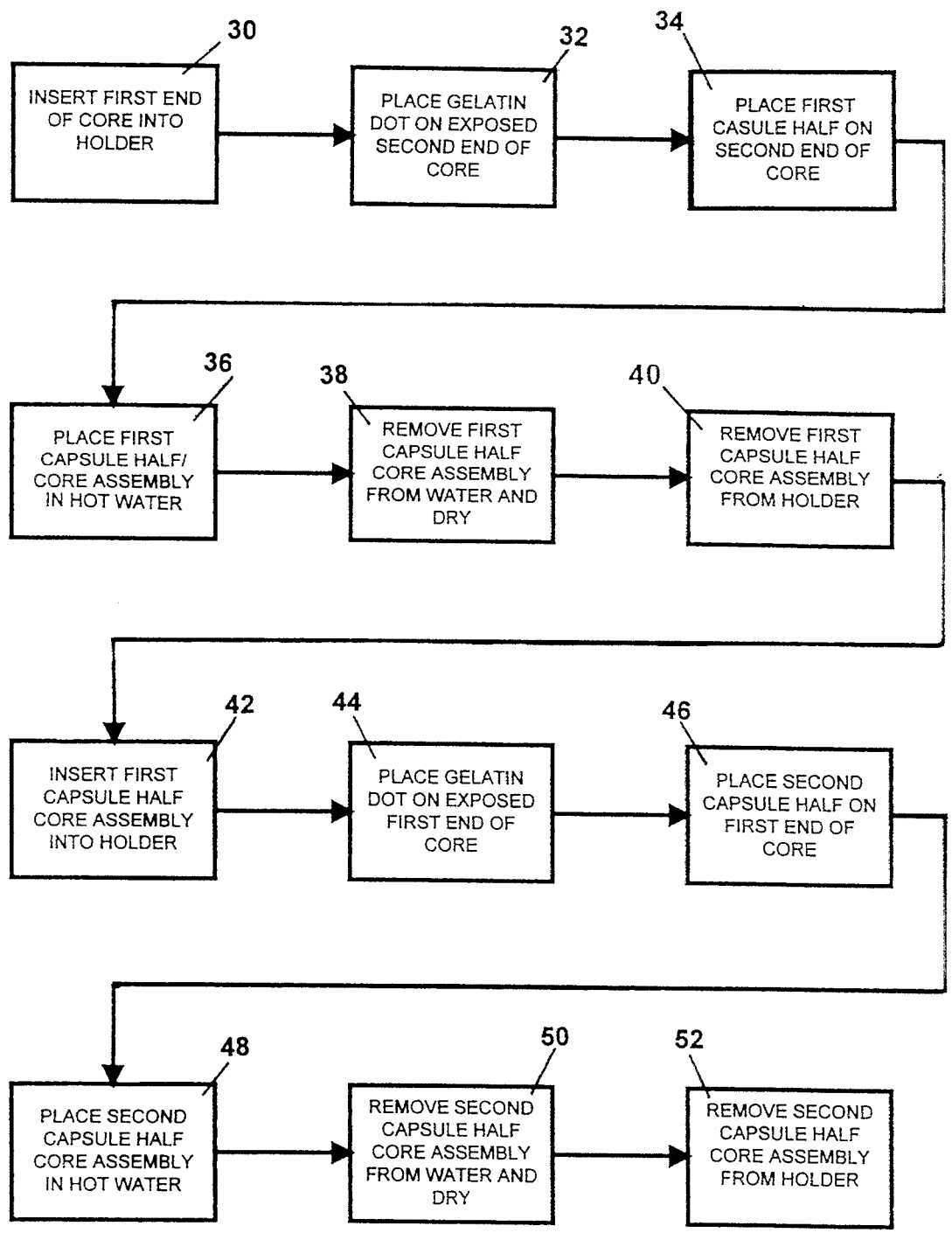
FIG. 3 is a diagrammatic view of the sequence for producing the shrink-wrapped hard-shell gelatin capsule covered caplet of the present invention.

FIG. 3 illustrates a diagrammatic view of the manufacturing sequence for producing the shrink-wrapped hard-shell gelatin capsule covered caplet of the present invention. With reference to the figures, in the manufacturing process a first end 13 of core 12 is inserted (block 30) into a holder (not shown) leaving a second end 15 of core 12 exposed. A dot of liquid gelatin 19 is then placed on exposed second end 15 of core 12, as shown by block 32. Hard-shell gelatin capsule half 16 is then placed over second end 15 of core 12 and into contact with gelatin dot 19 (block 34) so that the shell is held in place on core 12 to form a first half-shell/core combination. The first combination is dipped (block 36) into a tank (not shown) of hot water (90–95 degrees C.) up to the annular edge of capsule half 16 for a period of about 4 seconds to allow the hard gelatin shell to hydrate and plasticize. Gelatin dot 19 is chosen to have a melting point of greater than the temperature of the water so that capsule half 16 can remain in place on second end 15 of core 12. After removal from the tank, hard-shell gelatin capsule half 16 is then permitted, and preferably caused, to dry (block 38) to cause hard-shell gelatin capsule half 16 to shrink to fit the form of second end 15 of core 12 to form a first shrink-wrap gelatin hard-shell covering/core combination. First end 13 of core 12 is then displaced from the holder (block 40).

The now covered second end of the first covering/core combination is then inserted into the holder (block 42) and a dot of liquid gelatin 18 is placed onto exposed first end 13 of core 12 (block 44). Hard-shell gelatin capsule half 14 is then placed (block 46) over first end 13 of core 12 and into contact with gelatin dot 18 so that the shell is held in place on core 12 to form a second half-shell/core combination. The second combination is then dipped (block 48) into the hot water bath to allow it to hydrate and plasticize. As with gelatin dot 19, gelatin dot 18 has a melting point temperature that is higher than the temperature of the water. The plasticized hard-shell capsule half 14 dries (block 50) and shrinks to fit the form of first end 13 of core 12 to form a second shrink-wrap gelatin hard-shell covering/core combination. The covering/core combination is then displaced from the holder (block 52).

After completion of the shrink-wrapping process, examination of the medicament reveals that the two hard-shell gelatin capsule halves 14 and 16 are substantially in intimate contact with core 12, i.e. capsule halves 14 and have been shrink-wrapped onto core 12. As shown in FIG. 2, shrink-wrapped capsule halves 14 and 16 sometimes do not abut at a point about midway of a longitudinal axis of the core. This is because capsule halves 14 and 16 may shrink upon completion of treatment which may cause them to pull back a few thousandths from each other at the middle of core 12. If this occurs, a standard gelatin "belly" band 17 can be added to core 12 to cover the gap between capsule halves 14 and 16 to facilitate the simulation of a gelatin capsule medicament.

The amount of time gelatin hard shell capsules halves 14 and 16 need to be in the hot water tank to plasticize depends on the pigments present in the capsules. For example, red pigments appear to be the softest formulations and require the shortest dip times. White capsule halves, on the other hand, are hard formulations and require relatively long dip times. Yellow and clear capsule halves require dip times which are between the dip times needed for red capsules and white capsules.

The proper level of hydration needed to plasticize particular gelatin hard shell capsules can be determined by routine experimentation. To minimize processing difficulties, however, it is anticipated that the level of hydration should be as little as possible while retaining the ability of the capsule to shrink upon drying.

Those skilled in the art to which this invention pertains will appreciate that the foregoing descriptions of presently preferred embodiments of various aspects of this invention are primarily illustrative and exemplary and are not exhaustive of all of the ways in which the invention can be embodied. Various modifications and alterations can be made to the products, formulations, procedures, and apparatus which has been described without departing from the scope of this invention, as defined by the appended claims.

The embodiments of the invention in which an exclusive property or privilege is claimed are defined as follows:

1. A medicament comprising:
   (a) a solid generally cylindrical caplet with a longitudinal axis and having a first and a second end at opposite ends of said longitudinal axis;
   (b) a first hard-shell gelatin capsule half shrink-wrapped on said second end of said caplet;
   (c) a second hard-shell gelatin capsule half shrink-wrapped on said first end of said caplet and abutting, but not overlapping, said shrink-wrapped first hard-shell gelatin capsule half wherein said first and second hard-shell gelatin capsule halves have substantially the same diameter.

2. The medicament of claim 1 wherein said first and second shrink wrapped capsule halves abut at about a midway point of said longitudinal axis of said medicament.

3. The medicament of claim 1 further including a pharmaceutically acceptable adhesive situated between each caplet end and the adjacent inner surface of said first and second capsule halves.

4. A medicament comprising:
   (a) a solid caplet having a first and a second end, said caplet comprising a generally cylindrical shape;
   (b) a first hard-shell gelatin capsule half of a first color shrink-wrapped on said second end of said caplet;
   (c) a second hard-shell gelatin capsule half, of a color different from said first color, shrink-wrapped on said first end of said caplet and abutting, but not overlapping, said shrink-wrapped first hard-shell gelatin capsule half at about a midway point of a longitudinal axis of said medicament wherein said first and second hard-shell gelatin capsule halves have substantially the same diameter.

5. The medicament of claim 4 wherein said first gelatin capsule half is red.

6. The medicament of claim 4 wherein said second gelatin capsule half is white.

7. The medicament of claim 4 wherein said caplet comprises a width and length, wherein said length is at least 2.5 times the width.

8. The medicament of claim 4 further including a pharmaceutically acceptable adhesive situated between each caplet end and the adjacent inner surface of said first and second capsule halves.

9. The medicament as defined in claim 1 and further including a gelatin band extending transversely around said caplet to overly the abutting ends of said hard shell gelatin capsule halves.

10. The medicament as defined in claim 9 wherein said first hard-shell gelatin capsule half has a first color and said second hard-shell gelatin capsule half has a color different than said first color.

11. The medicament as defined in claim 4 and further including a gelatin band extending transversely around said caplet to overly the abutting ends of said hard shell gelatin capsule halves.

* * * * *